United States Patent
Crescenzo et al.

[11] Patent Number: 6,037,767
[45] Date of Patent: Mar. 14, 2000

[54] METHOD AND DEVICE FOR MAGNETICALLY TESTING PRODUCTS WITH A WALL COMPRISING AT LEAST ONE LAYER OF MAGNETIC MATERIAL

[75] Inventors: Eric Crescenzo, Gergy; Philippe Lembeye, Rouen, both of France

[73] Assignee: Coflexip, Paris, France

[21] Appl. No.: 08/983,547

[22] PCT Filed: Jul. 2, 1996

[86] PCT No.: PCT/FR96/01018

§ 371 Date: Jan. 8, 1998

§ 102(e) Date: Jan. 8, 1998

[87] PCT Pub. No.: WO97/03353

PCT Pub. Date: Jan. 30, 1997

[30] Foreign Application Priority Data

Jul. 10, 1995 [FR] France ................................. 95/08635

[51] Int. Cl.$^7$ ............................. G01N 27/82; G01R 33/12
[52] U.S. Cl. ............................................ 324/220; 324/240
[58] Field of Search ................................... 324/219, 220, 324/221, 227, 232, 238, 239, 240

[56] References Cited

U.S. PATENT DOCUMENTS

| | | | |
|---|---|---|---|
| 4,549,581 | 10/1985 | Unno et al. | |
| 4,700,134 | 10/1987 | Scharton et al. | 324/220 |
| 4,867,205 | 9/1989 | Bournazel et al. | |
| 5,336,998 | 8/1994 | Watts et al. | 324/235 |
| 5,359,939 | 11/1994 | Watt | 104/138.2 |

FOREIGN PATENT DOCUMENTS

| | | |
|---|---|---|
| 0431142B1 | 12/1992 | European Pat. Off. |
| 2193810 | 2/1988 | United Kingdom |

*Primary Examiner*—Walter E. Snow
*Attorney, Agent, or Firm*—Ostrolenk, Faber, Gerb & Soffen, LLP

[57] ABSTRACT

Products with a wall (1) comprising at least one layer (11) of ferromagnetic material may be tested by magnetising said layer using magnetising means (30) to generate therein a remanent magnetisation (H) parallel to the wall surface, then moving magnetic field sensors (2) along the wall and measuring, in the presence of said remanent magnetisation (H) alone, the magnetic field adjacent to the product surface, whereby changes in the field measured along said wall indicate defects (22) in said layer of magnetic material. The method is particularly suitable for testing elongate products in which the layer to be tested is not on the surface. Specifically, the method is suitable for testing pipelines or tubes for transporting petroleum.

10 Claims, 5 Drawing Sheets

METHOD AND DEVICE FOR MAGNETICALLY TESTING PRODUCTS WITH A WALL COMPRISING AT LEAST ONE LAYER OF MAGNETIC MATERIAL

The present invention relates in a general way to the magnetic inspection of objects or products which form or include a wall comprising at least one layer of magnetic material, in particular steel, for the purpose of detecting faults, such as cracks, in such products.

This type of inspection falls into the category of non-destructive inspection, for which there are already known inspection techniques involving the measurement of the leakage flux or the dispersion flux, and so-called eddy-current inspection techniques, which are used in particular for detecting faults in ferrous products.

The present invention is aimed particularly at the inspection of long, elongate products, the layer to be inspected of which is not directly accessible to the inspection equipment, or the faults to be detected of which lie within the thickness of the wall of the product, at a relatively large distance from that surface of this wall which is accessible to the inspection equipment. Such products may have a solid general cross-section, such as cables, in particular those coated with one or more protective or reinforcing sheaths, the inspection of which is carried out from the outside, or they may have a hollow cross-section, such as tubes, pipes, flexible pipes etc., the inspection of which may be carried out from the outside or from the inside. It is pointed out that the term "long products" should be understood to mean any elongate product whose length is such that it is practically impossible to access both of its ends simultaneously in order to completely magnetize the product without moving the magnetizing means, or that the power necessary for carrying out such a complete magnetization would be too great to be realized on an industrial scale.

The present invention is aimed in particular at the inspection of rigid or non-rigid tubular products for which the inspection must be carried out from the inside of the product. Such an inspection carried out from the inside proves to be necessary in particular for substantially rigid or flexible conduits, such as the pipes or pipelines used in the offshore oil production industry. This is because the in situ inspection of such conduits from the outside is often made almost impossible because of their environment. For example, the semi-rigid pipes or the flexible pipes used for transporting oil from a wellhead lying on the sea bed up to a surface drilling platform are usually equipped with connection means at their ends and with intermediate support means, such as floats, which prevent any accessibility from the outside. Now, it is precisely these connection or support regions which are subjected to the greatest stresses, and therefore exposed to the greatest risk of the appearance of cracks, crazes or fractures. Moreover, it is in these highly-stressed regions that other faults, such as pinholes or corrosion, may involve the greatest risks of cracking and of reduction in the mechanical strength of the pipes. However, these pipes conventionally include at least one internal sealing layer or an internal protective coating which means that the magnetic layer to be inspected is not directly accessible.

Although the invention is of general application to any product having at least one layer of ferromagnetic material, it is of particular advantage for products whose structure prevents or complicates the implementation of conventional inspection methods. Its aim is particularly to allow the inspection of the rigid, semi-rigid or flexible pipes used in the oil industry, which will be taken hereafter as a typical example of the application of the procedure and of the device according to the invention.

The rigid or semi-rigid pipes used for transporting oil generally consist of a steel tube which has a relatively large wall thickness and is often internally coated with a layer of a polymeric synthetic material, for example polyethylene, several millimetres in thickness. Furthermore, there is a tendency to use steel pipes of increasing thickness, this possibly being as much as or exceeding 30 mm and even 40 mm, thereby increasing the difficulty of inspecting them.

The flexible pipes have a more complex structure, their wall being formed from several superimposed layers intended to provide, on the one hand, sealing and, on the other hand, mechanical strength, both in the axial direction of the flexible pipe and in its radial or circumferential direction. These flexible pipes, like the one shown by way of example in FIG. 1 of the appended drawings, include in particular a pressure vault 11 consisting of at least one metal wire, for example, made of ferromagnetic carbon steel, which is spiralled with a short pitch, the function of which pressure vault is to withstand the circumferential component of the internal pressure forces exerted by the oil, and a plastic sheath 12, made of a non-magnetic and non-conductive polymer material, placed inside the pressure vault and bearing on the latter, in order to ensure that the flexible pipe is fluidtight. The thickness of the sheath is generally about from 5 to 10 mm, but it may be as much as 20 mm.

The vault may be formed by a single spiralled wire having a special profile, for example such as the one known by the name zeta profile and described in FR-A-2,182,372, designed to allow self-interlocking of the successive turns while allowing a little freedom of movement between two successive turns in order to ensure flexibility of the pipe. The vault may also be formed from two plies of wire, one turn of wire of one ply interlocking with two adjacent turns of the other ply. The two plies may thus be formed with a "U" profile, these wires being reversed from one ply to the other, as described in U.S. Pat. No. 4,549,581, or, in a similar manner, from wires having a "T"-shaped cross-section, as described in EP-A-431,142, or else one ply formed from wires having a "T"-shaped cross-section and the other formed from wires having a "U"-shaped cross-section, as described also in EP-A-431,142.

The thickness of this vault varies, depending in particular on the diameter of the flexible pipe and on the profile of the wires used, from a few millimetres to more than 15 mm.

Generally, an internal carcass 13, formed from a profiled tape which is interlocked and spiralled with a short pitch, lies on the inside of the plastic sheath in order to withstand any crushing forces on the flexible pipe and to support the plastic sheath in order to prevent the latter from collapsing inwards should there be a decrease in the pressure inside the flexible pipe. This carcass, the total thickness of which may vary from a few millimetres to 15 mm or more, is usually formed by a tape made of austenitic stainless steel, such as the grades 316/316L or 304/304L, which is non-magnetic or slightly magnetic.

Moreover, armouring plies 14, consisting of steel wires spiralled with a long pitch, surround the pressure vault and are intended essentially to withstand the axial tensile forces which are generated by the internal pressure, the dead weight of the flexible pipe and the oil which it contains, etc. These armouring wires may have various cross-sectional shapes, for example generally rounded or rectangular crosssections, in which case the wires are simply placed beside each other in the ply; or cross-sections of the interlockable type, such as "U"-shaped or "T"-shaped zeta-type cross-sections, similar to the vault wires described above and known, in particular, from EP-A-489,896. An external sheath 15 made of a thermoplastic protects the pressure vault and the armouring plies from corrosion.

These flexible pipes may also have a slightly simpler structure, the armouring ply or plies also providing resistance to the circumferential forces of the internal pressure and therefore replacing the pressure vault layer, or conversely a more complex structure, for example with a ply of short-pitch spiralled and interlocked wire, in a similar way to the vault described previously, placed around the armouring ply or plies, as described in particular in EP-A-147,288 and U.S. Pat. No. 4,867,205.

As will have been understood, the structure of these flexible pipes is complex and the existence of several layers of different materials and shapes makes them particularly difficult to inspect.

Similar problems arise in the inspection of other products of complex structure, such as cables and, in particular, the cables or braces used for the vertical anchoring of positive-buoyancy oil platforms, which include, in particular, an external sheath made of polymer material and/or one or more layers, surrounding the cable proper, made of a metallic material which is non-magnetic, weakly magnetic or even appreciably magnetic.

Among the various types of magnetic inspection techniques known, those using eddy currents, which can be used for electrically conducting materials, consist in generating, eddy currents in the inspected product which in their turn generate a variable reactive magnetic field which has an influence on the impedance of a receiving coil placed near the surface of the product. In the presence of a fault in the product inspected, the flow of the eddy currents is disturbed by this fault, thereby causing variations in the reactive field and therefore in the impedance of the receiving coil. The presence of faults in the product may therefore be detected by measuring the impedance.

However, this technique is not satisfactory in the case of the aforementioned pipes. This is because, in the case of internally coated rigid or semi-rigid pipes, the thickness of the internal coating layer or layers means that the sensor having the transmitting and receiving coils is at some distance from the metal wall to be inspected. Although the internal coating is non-conducting, this distance leads to a reduction in the sensitivity which is even more problematic when it is desired to detect faults which do not emerge directly at the internal surface of the metal wall (for example inclusions).

To these drawbacks should be added, in the case of flexible pipes, for example in the case of the inspection of the pressure vault, the problems due to the nature of this layer and to the presence of the internal carcass. The fact that the layer to be inspected is formed from one or more spiralled wires is a serious problem for inspection using the eddy-current technique which, as is known, is disturbed by irregular surface states in the product to be inspected. Moreover, the presence of the internal carcass further increases the distance between the sensor and the layer to be inspected.

In addition, even if the material of which the carcass is composed is non-magnetic or only slightly magnetic, it is electrically conducting. If the thickness of this conducting layer becomes greater than a few millimetres, the sensitivity of detection of faults lying in the magnetic layer to be inspected suddenly decreases, almost exponentially as a function of the thickness of the intermediate conducting layer because of the skin effect.

In order to limit the skin effect of the eddy currents and to ensure sufficient penetration of these currents into the pressure layer through the carcass, it would be necessary to work at low frequency, for example below 1000 Hz, or else in pulsed excitation mode with wide pulses of high intensity. In order to compensate for the drop in sensitivity due to the use of a low frequency, it would be necessary to use detecting coils which have a large number of turns, and which are therefore more bulky, and this would result in a decrease in the spatial resolution to the detriment of the detection of small faults and of the discrimination between two neighbouring faults. Moreover, pulsed excitation of high intensity requires making the excitation coils larger.

An additional drawback in the use of the eddy-current inspection technique arises from the specific structure of the layer making up the carcass, as may be seen in FIG. 2. This is because disturbing signals are inevitably generated by the eddy currents created in the conducting carcass because of the skin effect. Even if their amplitude may be diminished to a greater or lesser extent compared to the fault signals coming from the layer to be inspected by working at low frequency, these signals constitute a major part of the overall signal picked up by the sensor, this being the more so if the intermediate layer formed by the carcass, lying between the sensor and the layer to be inspected, has a complex geometry, a source of such disturbing signals. It follows that these disturbing signals coming from the carcass may disturb or mask the fault signals from the pressure layer, preventing any valid inspection of the latter. Multifrequency eddy-current processing allows, a priori the disturbing signal coming from an internal carcass to be filtered out, but such processing is not operational in the case of random irregularities, of the crack type, in the carcass. Suitable filtering of the signal received by the sensor, based on the periodicity of the geometry of the carcass could, a priori, make it possible to extract from the overall signal its component representative of the faults in the pressure layer; but because of the deformations of the flexible pipe, this periodicity is not uniform either and, in addition, such signal processing does not allow elimination of the signals coming from specific faults or irregularities in the tape.

The drawbacks mentioned above, due to the presence of the carcass and to its electrical conductivity, are further accentuated, as will be readily appreciated, if its constituent material is not non-magnetic or if it is actually magnetic or has irregularities in its magnetic characteristics.

Another technique known in a general manner in magnetic inspection is inspection using the measurement of the leakage flux or of the dispersion flux. This technique consists in generating a magnetic field in the product and in measuring directly the intensity of the field near the surface of the product. Conventionally, this type of inspection is used on ferromagnetic materials. The field lines are set up in the magnetized product along a direction which is generally parallel to its surface, In the presence of a fault, these field lines are deflected and tend to leave the product, and may thus be detected by measuring the local field in line with the fault.

An application of this pipeline inspection procedure and a device for its implementation are described, in particular, in document FR-A-2,229,970. The magnetization and detection modules described in this document is composed of several magnetic assemblies distributed circumferentially in order to scan the entire internal surface of the pipeline, by moving the said module along the latter. Each of these assemblies includes a magnet, the north and south poles of which are held close to the wall, and a detector consisting of magnetoresistive diodes is also placed near the wall between the two poles of the magnet.

According to the known method of measuring the leakage flux, it is customary to work close to magnetic saturation, that is to say that the field generated in the product is close to the maximum possible, so as to try to amplify as much as possible the perturbations created by the presence of faults in order to make them more easily detectable.

Compared to the eddy-current inspection method, the leakage-flux measurement has the advantage of being less sensitive to the presence of a conducting, but non-magnetic, intermediate layer between the sensor and the wall to be inspected insofar as, however, this intermediate layer does not lead to an excessive distance of the sensor from the said wall. This is because such non-magnetic electrically conducting layers theoretically constitute, in the case of a constant magnetic field, a simple air gap through which the lines of flux pass without them being disturbed, even if these layers have irregularities or a complex geometry.

However, if the cumulative thickness of the intermediate layers exceeds a value of about 10 mm, this method proves to be almost inapplicable, on the one hand because it would be necessary to use a very intense generating field in order to succeed in saturating the layer to be inspected, thereby causing a first problem with regard to the means necessary for generating this intense field. In addition, since the detector used is also necessarily at some distance from the surface of the wall to be inspected, the relative field variations caused by the faults become very small since the deflections of the flux lines caused by the leakage flux become increasingly spread out on going away from the fault which is the cause thereof. The detector is therefore in a situation of having to measure very small variations in an intense field, which the currently known sensors are not capable of doing. This problem is further aggravated by the fact that, since the poles of the generator magnet are themselves some distance away from the surface of the layer of magnetic material to be inspected, there is a direct loop in some of the field lines between the two poles of the magnet in the space between the poles and the surface of the wall to be inspected and therefore, in particular, just at the point where the detector is placed. These field lines are not, in principle, disturbed by the medium through which they pass, since this medium is non-magnetic. However, in contrast, since these lines are not channelled by a magnetic material, they reflect any possible original variations in the field, which are therefore detected by the detector. It will be noted that these variations in the original field are even more likely to occur when the source is an electromagnet, a situation which becomes almost indispensable in order to create the high-intensity fields required.

The problems mentioned above in the context of the inspection of a flexible pipe from the inside also arise in the case of the inspection from the inside of other products having a wall of complex structure, or in the case of the inspection from the outside of such tubular products or of products having a solid section, such as the cables or similar products mentioned previously, or else of flat products such as sheets, or of products with walls of any shape, such as tanks or vessels.

A procedure is also known, from document U.S. Pat. No. 5,336,998, for detecting faults in pipes manufactured using the well-known process of centrifugal casting, in which procedure a magnetic field is created in the pipe by passing a heavy DC current through a conductor placed axially along the pipe. Next, after having removed the conductor, a row of detectors is placed along the pipe and the latter is rotated so that the detectors, during this rotation, detect any flux leakages caused by faults and resulting from the remanent magnetization remaining in the pipe. However, this procedure can only be used for pipes of limited length since the magnetizing step requires being able to access both ends of the pipe and the measuring step requires rotating a pipe about itself and, in addition, it requires a very high power in order to effect complete magnetization of the pipe. This procedure is therefore not suitable for the inspection of the long products envisaged by the invention.

The object of the invention is to solve the above problems and is aimed in particular at improving the reliability of detecting faults in long products in which the layer to be inspected is not directly accessible to the inspection means, in allowing the detection of faults lying deep within the wall of the product to be inspected, whether these faults be themselves far from the surface of the layer of magnetic material to be inspected or whether they be only far from the measuring tool because of intermediate layers between the latter and the layer to be inspected, and is also aimed at obtaining the maximum amount of information characteristic of the faults detected in a single inspection operation.

With these objectives in mind, the subject of the invention is a procedure for the magnetic inspection of long products, in particular of tubular products such as pipes, the wall of which includes at least one layer made of a ferromagnetic material, in which the said layer is magnetized by a field oriented parallel to the surface of the said wall, a magnetic-field detector is moved along the wall and the magnetic field near the accessible surface of the product is measured, variations in the measured field (along the wall) being indicative of faults affecting the said layer, characterized in that the magnetizing step is carried out by moving, longitudinally with respect to the said product, magnetizing means which create a localized magnetization field, so as to generate a remanent magnetization in the said layer, and in that the measurement is carried out on the run after the said magnetizing step, just in the presence of the said remanent magnetization.

The procedure according to the invention makes it possible to improve considerably the detection of faults affecting elongate products, in particular when their wall is thick and/or composed of several superposed layers and when the faults to be detected lie within a layer not directly in contact with the accessible surface of the product.

This is because the measurement made only in the presence of a remanent magnetization in the ferromagnetic layer to be inspected makes it possible to detect even very small variations in the field, in particular in the internal space of the product, near its accessible surface, since these small variations caused by faults are the only field manifestations detectable on the outside of the wall, all the field lines being otherwise contained within the ferro-magnetic material of the layer to be inspected, since only the remanent magnetic field remains at the time of measurement.

In particular the procedure makes it possible to obviate all the perturbations which may be caused by the magnetizing step, because the latter takes place before the measurement, either by firstly moving the magnetizing means in order to magnetize the entire product on the run and then moving the measuring means, independently of the said magnetizing means, in order to take the measurement, again on the run, or, in particular when the products are very long, by simultaneously moving the magnetizing means and the measuring means, but the latter then being sufficiently distant to the rear of the magnetizing means in order not to be subject to their direct influence.

Another advantage of the procedure according to the invention is that it improves the detectability of fatigue cracks. This is because the remanent field is very sensitive to local variations in certain metallurgical properties, such as the hardness, which are associated with anomalies in certain magnetic properties of the material, such as the coercive field, the remanent induction and the magnetic anisotropy. Now, a fatigue crack is characterized in particular by a high hardness of the two lips of the crack. Thus, in such a case, the fault signal due solely to the geometrical accident which the crack constitutes is increased by the signal due solely to the local variations in the magnetic properties, which consequently increases the detectability of such fatigue cracks.

It will also be readily understood that the procedure according to the invention makes it possible to get round all the problems indicated previously in eddy-current inspection since, at the time of measurement, the field present is fixed and constant and therefore not likely to generate such currents which in turn generate variations in the field over time.

Preferably, before magnetizing the said layer, the wall is demagnetized. Thus, before the magnetizing step, the most homoceneous magnetic state possible is established, since this is substantially free of any magnetism, throughout the thickness of the wall, not only in the layer to be inspected but also in any other layer capable of magnetization, whether homogeneous or not. As a result, the magnetic state obtained after the magnetizing step is also the most homogeneous as possible since it results from this single intentional magnetizing step and is independent of the magnetic history of the product before its inspection. Moreover, this prior demagnetization makes it possible to carry out the magnetizing step without reaching complete magnetic saturation of the layer to be inspected, which, otherwise, would be desirable in order to obtain sufficient homogeneity of the magnetic state of the product.

It will be noted in this regard that the demagnetization step thus makes it possible to use less powerful magnetizing means, and fewer consumers of energy when these means are electromagnets.

According to another preferred arrangement, in respect of the application of the procedure to the detection of faults in a product whose wall includes, between the layer to be inspected and its accessible surface, an intermediate layer which is not completely non-magnetic, the said intermediate layer is selectively demagnetized after the said magnetizing step. This selective demagnetization, carried out at a defined frequency depending on the thickness and on the nature of the intermediate layer, taking into account the skin effect, in order to affect as little as possible the magnetic state, obtained by the prior magnetizing step, of the layer to be inspected, makes it possible to eliminate any field variations which would be caused by the presence of a remanent field in an intermediate layer which is not completely non-magnetic or which has irregularities in the magnetic properties of this layer.

In a general manner, the procedure, the object of which is to detect faults via variations in the remanent field which are caused by these faults, consists:

in creating a remanent field in the product in such a way that the range of the possible remanent field in the intermediate region is less than that of the remanent field in the region to be inspected at the point where the fault which is to be detected lies and in placing at least one sensor at a position outside the range of the remanent field in the intermediate region, while still being sensitive to the remanent field characteristic of the fault to be detected.

The range of the remanent field in the intermediate region may be affected by possible imperfections in the selective demagnetization or by the irregularities in the remanent field in the intermediate region if its average strength is low, and in this case inspection is carried out without selective demagnetization.

One particular method for implementing the invention thus consists in placing a sensor at a distance from the accessible surface such that the sensor remains within the range of the field characterizing the fault to be inspected and outside the range of the remanent field in the intermediate region. Because the optimum distance from the accessible surface may vary depending on the region inspected (for example depending on the position along the length of the pipe) and depending on the fault and small variations in the characteristics of the wall, it is possible to carry out the procedure in two different ways:

by placing at least two sensors at different distances from the accessible surface so that at least one sensor is at the correct distance;

or by moving the sensor in order to bring it to the desired position, this being possible if the inspection operation is carried out not continuously, while the measuring device is being moved, but with the latter stationary, the device being progressed in a series of stationary inspection steps and of elementary phases during which it is moved between two successive inspection steps.

The subject of the invention is also a device for the implementation of the above procedure. This device, which includes magnetizing means suitable for generating, in the wall of the product, a magnetic field oriented parallel to its accessible surface, and means for measuring the field near the said surface, the magnetizing means and the measuring means being suitable for being moved parallel to the said surface, is characterized in that the magnetizing means are arranged so as to generate a localized magnetization field and in that the magnetizing means and the measuring means are, while they are being used, separated from each other by a distance such that the magnetic field generated by the magnetizing means is not directly measurable by the said measuring means.

The magnetizing means and the measuring means may be moved along the surface of the product successively and independently of each other, or simultaneously, as long as they are sufficiently far apart from each other so that the measuring means are not influenced by the field emitted by the magnetizing means.

Preferably, the measuring means include sensors placed so as to measure the magnetic field in several directions at each measurement point, thereby making it possible, at each point, to obtain the value of the various spatial components of the field and their variations depending on each other and depending on these directions. Consequently, it is possible not only to locate the faults but also to characterize them and, using suitable processing of the measurement signals, to eliminate any information with regard to spurious faults resulting, for example, merely from the geometry of the layer to be inspected.

Other characteristics and advantages will appear in the description which will be given, solely by way of example, of a device according to the invention for the inspection of oil transmission pipes.

Reference will be made to the appended drawings in which.

Figure 1:
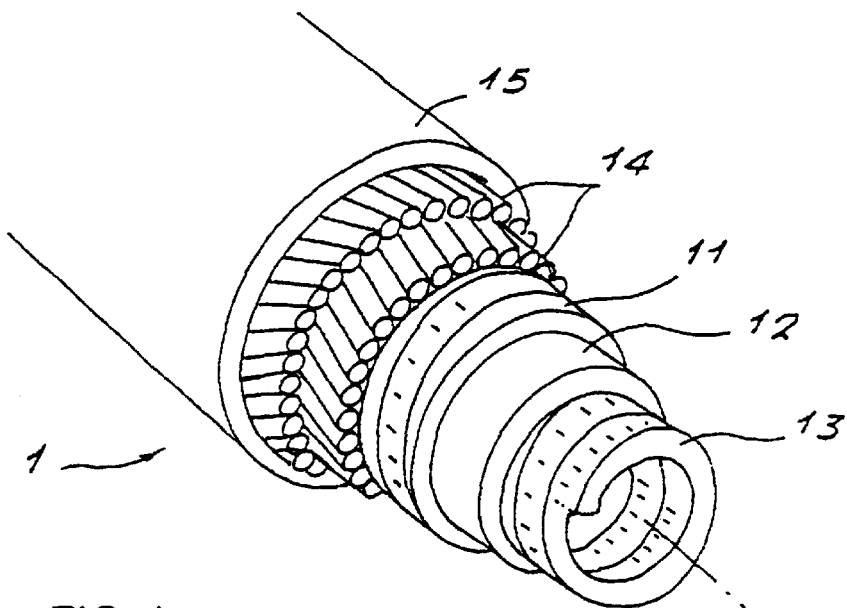
FIG. 1 is a perspective view of a portion of flexible pipe used for oil transmission.
Figure 2:
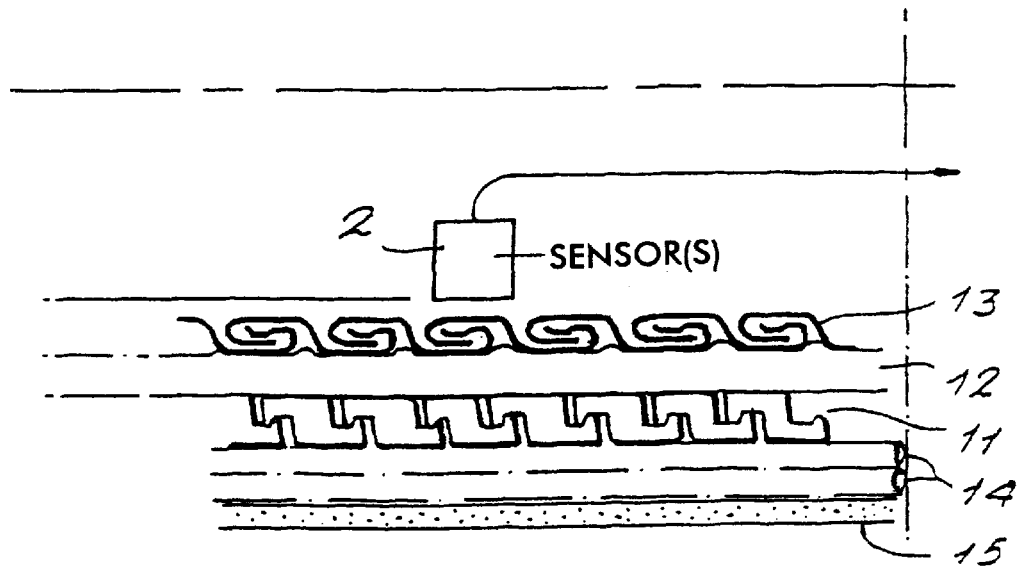
FIG. 2 is a partial sectional view of the wall of this pipe.

The drawings in FIGS. 1 and 2 show a typical example of a flexible pipe having a wall 1 of complex structure, already described at the beginning of this specification. The inspection of such a flexible pipe requires, in particular, the detection of faults in the pressure vault 11 which is particularly at the core of the wall, between, on the one hand, the sealing sheath 12 and the internal carcass 13 and, on the other hand, the armouring layers 14. It is clearly apparent from FIG. 2, which shows a longitudinal section of the wall 1, that the inspection of the flexible pipe from the inside means that the inspection means, and in particular the measurement sensor or sensors 2, are relatively far away from the vault 11 to be inspected, by a distance at least equal to the cumulative thickness of the sheath 12 and of the carcass 13, which may be as much as 20 mm or more.

Figure 3:
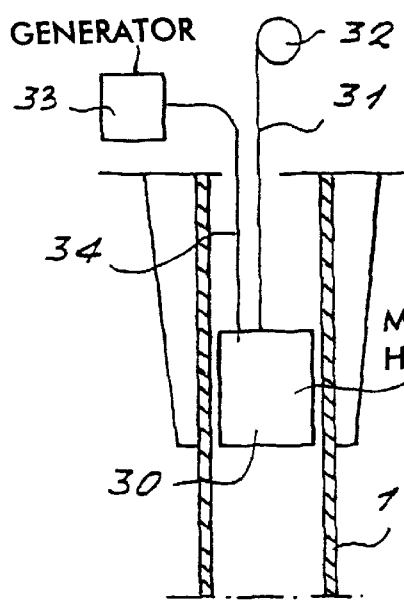
FIGS. 3 and 4 represent diagramatically the two successive steps, the magnetizing step and the measuring step, carried out during inspection of one end of a vertical pipe, such as the end, connected to a drilling platform, of an oil extraction pipe.
Figure 4:
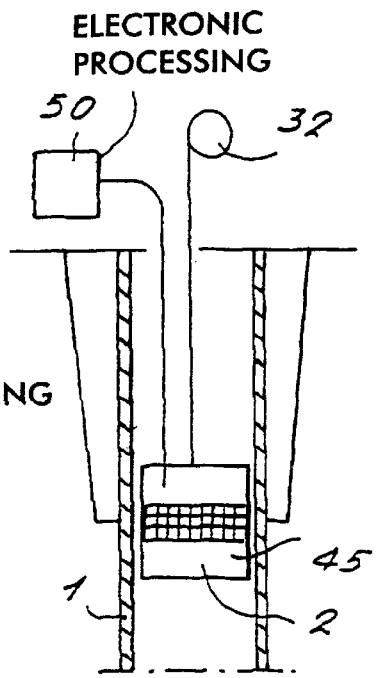
Figure 5:
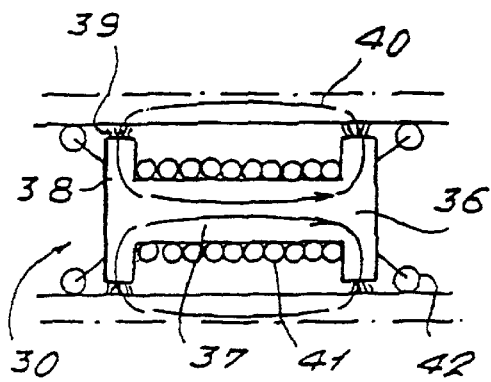
FIG. 5 represents a first embodiment of the magnetizing means.

The drawings in FIGS. 3 and 4 show diagramatically the device used for inspecting the vault 11 near the connection of the flexible pipe to an oil platform. The device includes driving means, such as a winch 32 for moving, alternately and successively, a magnetizing head 30 or a measuring head 45, these being supported by the cable 31 of the winch 32. The magnetizing head, shown diagramatically in FIG. 5, has a magnetic yoke 36, for example made of laminated iron-silicon steel alloy, formed by a central core 37 which extends axially and by two disc-shaped end portions constituting the poles 38 of the magnetic circuit. In order to direct as well as possible the flux lines 40 towards the layer to be magnetized, the perimeter of the poles 38 is provided with flexible elements which conduct the magnetic flux lines, such as metal brushes 39, which may thus be held in contact with the internal surface of the flexible pipe even in the case of slight variations in its internal cross-section. A solenoid 41 is wound around the core 37 and connected to a generator 33 via an electrical power cable 34. The magnetizing head is moreover centred in the flexible pipe by rollers 42. Such a magnetizing head is used to generate an axial magnetization in the flexible pipe which is conducive to the detection of cracks oriented perpendicular to the axis. Other magnetizing means may also be used, for example to create a circumferential magnetization transverse to the axial direction or a multidirectional magnetization, such as those, for example, described in document EP-A-0,639,839 or means which in their principle are equivalent.

Figure 6:
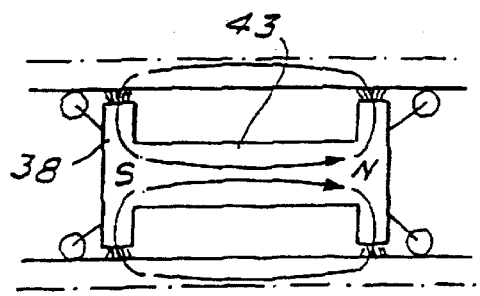
FIG. 6 represents a second embodiment of the magnetizing means.

In an alternative form of the embodiment of the magnetizing head shown in FIG. 6, the electromagnet formed by the solenoid 41 and the core 37 may be replaced by a permanent magnet 43. Such an alternative embodiment makes it possible to dispense with the use of the generator 33.

In a first phase of the inspection, the magnetizing head is lowered into the flexible pipe 1 as far as the lower end of the region to be inspected and the generator 33 is then switched on, this generator supplying the magnetizing head which is then raised at a constant speed by means of the winch 32 as far as the upper end of the flexible pipe. During this rise, the ferromagnetic layer or layers in the wall of the flexible pipe are magnetized and retain a remanent magnetization after the magnetizing head has passed along the pipe.

Figure 7:
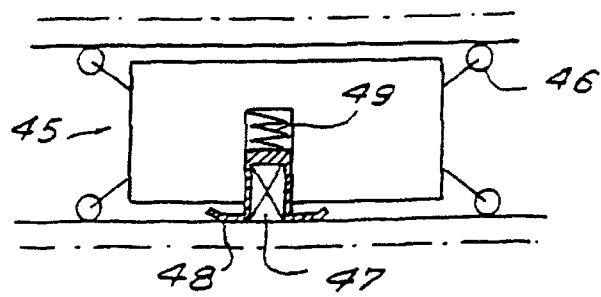
FIG. 7 represents diagramatically the measuring means.

Once the magnetizing head has been removed from the flexible pipe, it is replaced by the measuring head 45 which is moved in the flexible pipe in a similar manner to the magnetizing head. This head, shown diagramatically in FIG. 7, includes the means for measuring the magnetic field and is guided in the flexible pipe by rollers 46. It includes one or more sets of sensors 47 applied against the internal surface of the wall 1 by a skid 48 and a pressure spring 49. It is connected to an electronic box 50 for processing the signal delivered by the sensors.

Once the measuring head has been lowered to the bottom of the region to be inspected, it may be raised at a constant speed, the measurements being made continuously during the rise, by sensors in a grid arrangement which are distributed in sufficient number around its periphery to inspect the entire crosssection of the flexible pipe. However, the sensors will be preferably mounted so as to be able to move in axial translation and in rotation about the axis of the measuring head and a suitable motor-drive means will provide precise movement of the sensors. In this case, the measuring head will be raised sequentially and immobilized between two successive movements, and the sensors are then moved with respect to the immobilized measuring head so as to scan the entire internal surface of the wall along the length of the measuring head. This alternative way of implementing the invention allows better detection, and better location of the faults detected.

In an alternative way of implementing the procedure, an intermediate selective partial demagnetizing step is carried out between the two magnetizing and measuring steps, the demagnetizing step being intended to demagnetize the layers lying inside the vault 11 to be inspected, such as the carcass 13, without, however, demagnetizing the layer to be inspected. The partial demagnetization is carried out so as to reduce the remanent magnetization of the intermediate region sufficiently for its influence on the measurement tool to become negligible compared to the influence of the faults in the region to be inspected.

For this purpose, a demagnetizing head 52 is moved along the flexible pipe, in the same way as the magnetizing and measuring heads.

Figure 16:
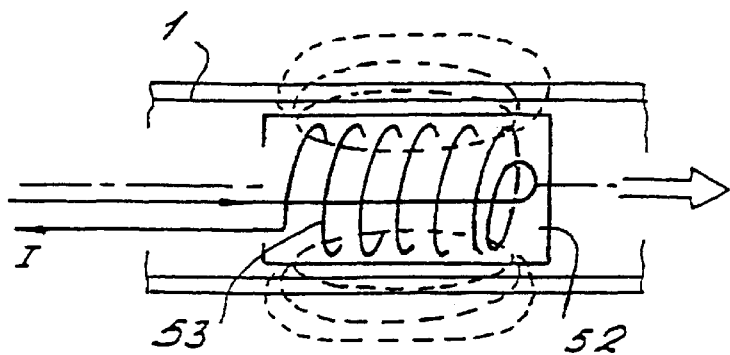
FIG. 16 illustrates the principle of a first embodiment of the demagnetizing means.

In a first embodiment, shown in FIG. 16, this demagnetizing head includes a solenoid 53 powered with alternating current of defined frequency and intensity so as to obtain the desired selective demagnetizing.

Figure 17:
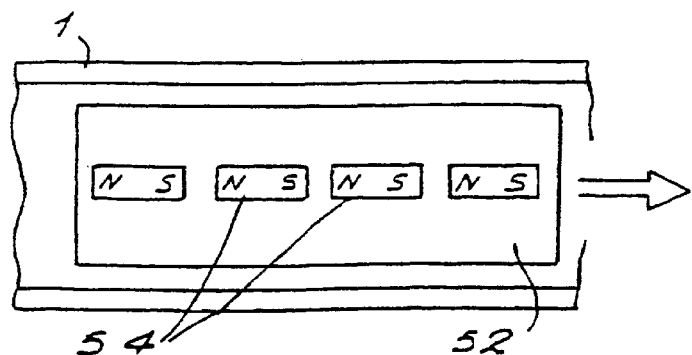
FIG. 17 illustrates a second embodiment of these demagnetizing means.

The demagnetizing head may also include, as shown in FIG. 17, instead of the solenoid 53 supplied with alternative current, a plurality of permanent magnets or of solenoids 54 supplied with direct current and arranged in groups oriented axially so that the flux lines from these magnets or solenoids 54 are in opposition, in pairs, and decrease from one axial end of each group to the other axial end, in the direction of movement of the demagnetizing head. The principle of such demagnetizing means or of other means which are again equivalent is described, in particular, in document EP-A-0, 639,839.

In another alternative way of implementing the procedure, a preliminary step of demagnetizing the flexible pipe is carried out before the magnetizing step, the purpose of the preliminary step being the prior homogenization of the magnetic state of the entire wall. This complete demagnetization may be carried out by means similar to those used for a partial demagnetization, but with stronger or lower-frequency magnetic fields in order to reach the layers in the wall which are furthest away from the demagnetizing head.

In the inspection method which has just been described above, the various magnetizing and measuring steps, and optionally the demagnetizing steps, are carried out successively in the order indicated, but independently of each other. Such a method is applicable in practice only when the pipes to be inspected are easily accessible over the entire length to be inspected, and therefore for short pipes or for the end regions of long pipes, because, in particular, of the mechanical and electrical connections to the equipment external to the pipe which are necessary.

Figure 15:
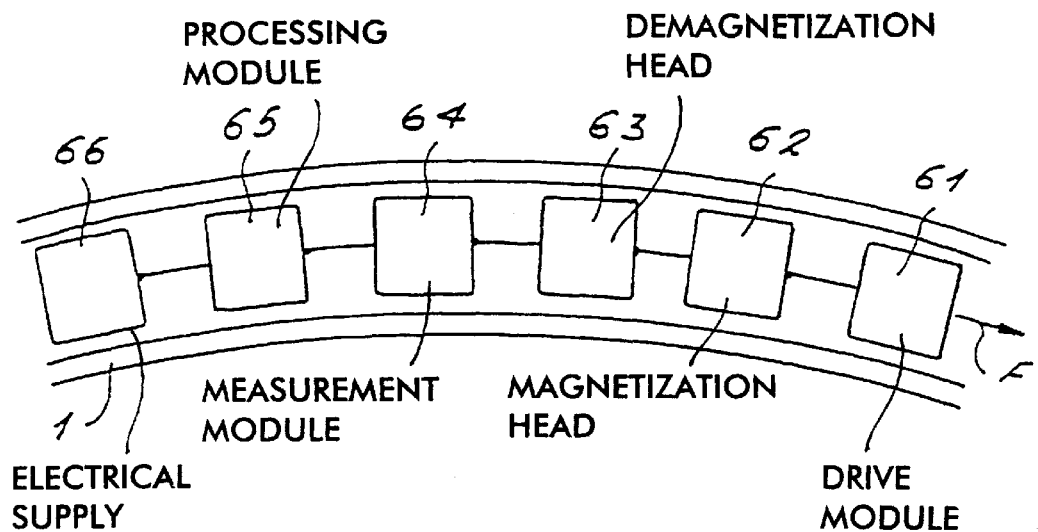
FIG. 15 represents diagramatically an alternative way of implementing the invention by means of an autonomous inspection device for inspecting long pipes.

In order to inspect a long pipe or regions of such pipes which are far from the ends, for example flexible subsea pipes which may be as much as or even longer than 1000 m, an autonomous inspection device will be used which can be moved along the pipe by its own means. FIG. 15 shows such a device, consisting of several modules 61 to 66 coupled to each other by articulated linkage elements 67 in order to allow the assembly to travel even around bends in the flexible pipe.

The first module 61 in the direction of movement shown by the arrow F is a drive module which may, for example, include mechanical drive means, which operate by contact with the internal surface of the flexible pipe, or sealing elements allowing propulsion by the liquid moved in the pipe so as to move all the modules inside the pipe simultaneously.

The second module 62 is a magnetization module having a magnetization head of the type described above, preferably equipped with permanent magnets in order to avoid having to use an additional energy source.

The third module 63 is a selective demagnetization module, also preferably equipped with permanent magnets.

The fourth module 64 is a measurement module carrying the sensors for measuring the remanent field, these being preferably arranged in an annular grid arrangement covering the entire circumference and in two rows so that the measurement areas of two adjacent sensors overlap.

The fifth module 65 is a module for processing and storing the signals delivered by the sensors and for measuring the position of the device in the pipe.

The sixth module 66 is a supply module comprising batteries for supplying electrical power to the other modules.

If prior complete demagnetization is necessary, an additional demagnetization module (not shown) is placed upstream of the magnetization module, i.e. on the other side of this module with respect to the measurement module.

The distance between the various modules, in particular between the measurement module 64 and the previous modules is sufficiently large so that the sensors in the said measurement module are not influenced by the magnetic fields of the magnetization modules 62 and the selective-demagnetization module 63. This distance is defined so that, in particular, at any moment, the magnetic field measured by the sensors remains identical to that which would be measured if the distance separating the measurement module 64 from the field-creating modules 62, 63 were to be considerably increased (for example by about 100 m), while leaving the measurement module stationary and moving the said field-creating modules.

Assemblies intended to be moved along pipes in an autonomous manner are already known and reference may be made, in particular, by way of example, to the description of such an assembly given in the document FR-A-2,229,970 already mentioned. The elements of general structure of the said modules and their linkage means may be easily adapted in a suitable manner by those skilled in the art, on the basis of already known equivalent devices.

In order to make the advantages of the procedure and of the device according to the invention more clearly understood, additional explanations will now be given about the specific aspects of the invention, taking as an example the inspection of flexible pipes of the type which are shown in FIGS. 1 and 2.

Figure 8:
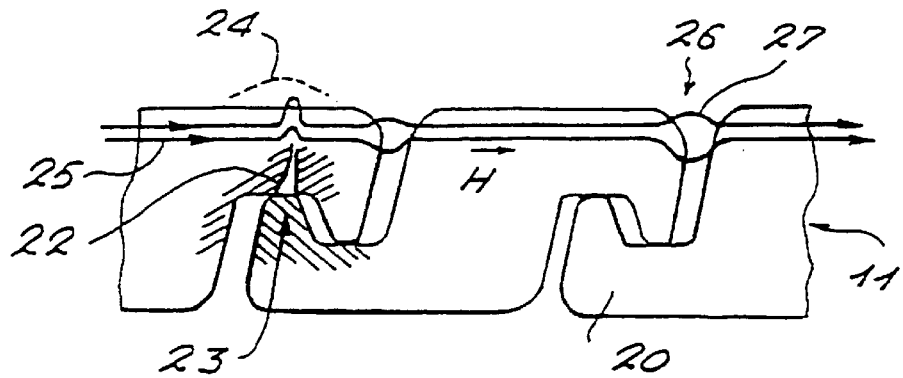
FIG. 8 illustrates the distribution of the field lines in the layer to be inspected of a flexible pipe, such as the one shown in FIG. 1, in the axial direction of the flexible pipe.
Figure 9:
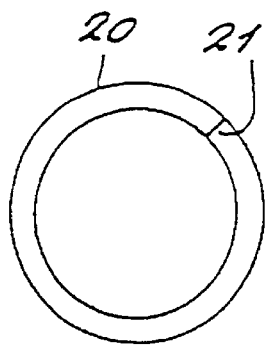
FIG. 9 shows, in cross-section, a crack oriented axially, such as a transverse crack or fracture in a short-pitched spiralled vault wire.

It should be pointed out that the faults which it is desired to detect in these flexible pipes are, in this case, essentially faults in the pressure vault 11 which, in the example in question, is produced by a zeta-type wire 20 which is spiralled with a short pitch and interlocked onto itself, as may be seen in FIGS. 2 and 8. The faults affecting this layer may be of various types:

transverse fractures 21 in the wire, these therefore being oriented approximately parallel to the axis of the flexible pipe, as shown in FIG. 9;

longitudinal cracks 22 in the wire, these therefore being oriented transversely with respect to the axis of the flexible pipe, as shown in FIG. 8;

unlocking of adjacent turns, etc.

It will be noted that the fractures 21 in the wire generally appear after the development of longitudinal cracks 22 which themselves appear essentially in the interlocking region 23, of smaller thickness, of the zeta profiled strip. Since a transverse fracture of the wire is a serious fault, priority will therefore be given to the detection of longitudinal cracks in the wire since these appear before the transverse fractures and, consequently, as will be more clearly understood below, preference will be given to axial-type magnetization of the flexible pipe, illustrated in FIG. 8, this being more suitable for detecting such cracks which extend transversely to the axis of the flexible pipe.

The prior demagnetization carried out before the layer to be inspected is magnetized makes it possible, as already seen, to homogenize the magnetic state of all of the layers in the wall. The magnetic field generated for this purpose must therefore be of high strength and of low frequency, for example approximately 50 Hz, so as to reach the layers furthest away from the inside of the flexible pipe, in order to prevent any residual magnetization remaining in certain layers before the magnetizating step creates variations in the remanent field after the magnetizing step.

However, on account of the large consumption of energy which may be necessary for this complete demagnetization, the latter may be dispensed with, in particular in the case of a very long pipe to be inspected by an autonomous device as described above, in order not to burden the device with a high-power energy source and to limit its operating range.

The magnetizing step must allow the creation of a remanent field large enough to allow subsequent detection of small faults and faults lying deep within the layer to be inspected.

The magnetization strength is adjusted so as to ensure that there is an optimum compromise between the two following phenomenon:

in order to maximize the level of remanent magnetization, it is necessary to reach at least the start of the bend in the magnetic saturation of the material of which the layer to be inspected is composed;

however, in order to minimize the normal components of the remanent field, which stem from the fact that the flux lines 40 of the magnetization field are approximately perpendicular to the inspected surface at the ends of the magnetizing head (see FIGS. 5 and 6), it is preferable not to increase the magnetization excessively.

By way of example, the magnetization strength will be about 4000 to 8000 A/m. In this case, the strength of the remanent field H at the surface of the layer to be inspected is typically between 500 and 2000 A/m and the variation in the strength of this field at a fault is typically within the 50 to 200 A/m range.

Selective demagnetization makes it possible to homogenize the remanent field which was able to be created during the magnetizing step in an internal layer which is not completely non-magnetic such as, in the example in question, the internal carcass 13, by reducing this field to its minimum value. This is because, although usually made of austenitic stainless steel, this carcass may, depending on the grades of steel used, be slightly magnetic and, moreover, the forming of the tape of which the carcass is composed may lead to heterogeneity in the magnetic properties in the cross-section of this tape. As a result, magnetizing the flexible pipe may lead to the creation of a remanent field in the carcass, which field is all the more susceptible to variations in the length of the flexible pipe because of the complex geometry of the said tape, because of possible irregularities in the winding pitch of the tape and because of the said magnetic heterogeneities.

By removing any remanent field from this carcass 13, the selective demagnetization prevents all these irregularities from being detected as faults during the measurement, or prevents them from generating signals which mask the true signals from faults in the pressure vault.

It will be noted that, in a similar way, this selective demagnetization makes it possible to demagnetize any intermediate layer between a layer to be inspected of a pipe and its internal space. It consequently makes it possible to inspect, in a pipe having several layers of magnetic material, a layer far from and separated from the inside by another layer of magnetic material or, in the case of a thick-walled rigid or semi-rigid pipe, to detect faults lying deep within this wall or towards the outside thereof, by obviating any geometrical or magnetic irregularities in the internal surface layer of this wall.

As indicated previously, this selective demagnetization must therefore be carried out with consideration of the geometrical structure of the flexible pipe, of the materials which make up its wall and of the characteristics of the layer which it is desired to inspect, and of the faults which it is desired to detect so as to optimize the appearance of the leakage flux caused specifically by these faults.

Once these magnetizing and selective demagnetizing operations have been carried out, the leakage flux may be detected and measured. It will be noted that the strength of the field which can be measured by the sensor is relatively low because of the large distance between the vault 11 and the sensor 2.

Figure 11:
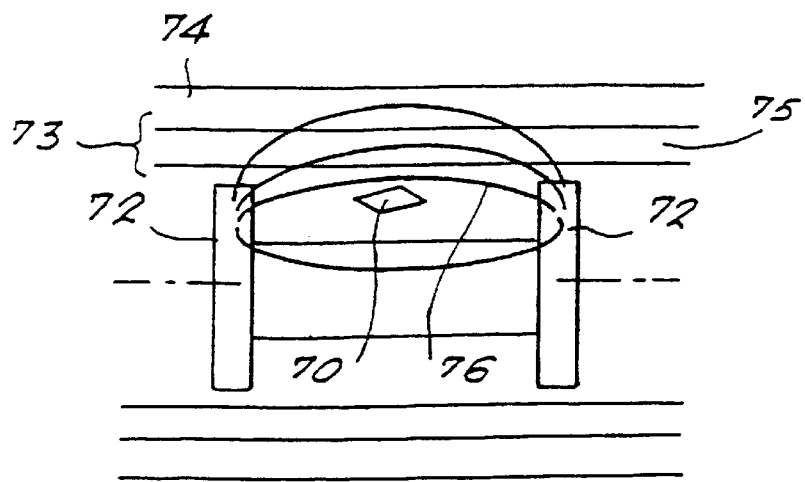
FIG. 11 represents diagramatically, by way of comparison, the distribution of the field lines in the case of an inspection of an internally coated rigid pipe using the leakage-flux method according to the prior art.

This is why, in the known methods of inspection using measurement of the leakage flux, it is desired to increase the strength of the field generated in the layer to be inspected in order correspondingly to increase the intensity of the leakage flux caused by the faults; and this is why, consequently, in these known methods, the sensor 70 is placed in the region where the field generated in the product is strongest, i.e. between the poles 71, 72 of the field source, as shown in FIG. 11 and described in document FR-A-2,229,970. However, this has the drawback, in particular when the air gap 73 between the said poles and the surface of the magnetic layer 74 to be analysed is large, as is the case, for example, with flexible pipes or with rigid pipes coated internally with a layer 75 of polymer material, that flux lines 76 are looped directly between the said poles. The sensor 70, lying between these poles, is directly exposed to this magnetizing flux which may be very intense compared to the leakage flux created by a fault and which, moreover, tends to smooth out the points of emergence of the leakage flux. Consequently, although the intensity of this leakage flux increases with that of the generating field, the measurable variations in this leakage flux are, in the end, small, of about 10 to 15 oersted (800 to 1200 A/m) compared to the total field existing at the sensor, which field may also itself be disturbed by variations, independent of the product to inspect, arising from the field generator itself.

The inventors have in fact discovered that, against all expectation, although the intensity of a leakage flux caused by a fault is from 10 to 20 times lower in the presence of a remanent field than in the presence of a field generated at the time of measurement, detection of the faults is considerably improved in the case of measurement carried out in the presence of just the remanent field. It will be noted that the typical amplitude of a fault leakage flux, measured in such a case with a small air gap of about 3 nmm, is about 1 oersted (80 A/m) and may become less than 0.1 oersted for larger air gaps of about 15 to 20 mm, for example. One explanation of this is that, although the measured fault signal is small, the noise in the signal is itself also very low because of the absence of an exciting field. In addition, the relative variation $\Delta H/H$ in the field to be measured is quite high since the field H at each point is solely due to the remanent field lines, to the exclusion of the magnetizing field.

Although various types of sensors can be used, for example Hall-effect sensors, it will be preferable to use, in order to compensate for the low intensity of the leakage flux, high-sensitivity high-resolution sensors, such as magnetoresistive devices or magnetodiodes mounted, again preferably, as a Wheatstone bridge, or else compact magnetometers, the principle of which is based on the non-linear effects of ferrites. Such sensors can be used to measure field variations of less than 0.1 or even 0.01 oersted and have a spatial resolution of a few tenths of a millimetre, with a frequency bandwidth of from 0 to a few thousands of hertz, allowing the detection of small faults even when the sensor is moved rapidly along the pipe, the speed of movement possibly varying, for example, from 0 to a few metres per second.

As shown, intentionally exaggerated, in FIG. 8, the deviations 24 of the flux lines 25, caused by the crack 22, become more spread out the further away from the said fault. A high spatial resolution makes it easier to detect faults far from the sensor by avoiding having to smooth out the response of the sensor to such a leakage flux.

One particularly suitable sensor, made using magnetoresistive devices connected as a bridge, is described in French Patent Application No. 93/15783, to which reference may be made, and the teaching of which, with regard to the sensor, is included for reference in the present application.

In order to improve the detection and identification of the faults, several sensors may be combined, these being arranged so that each measures one spatial component of the field at the point of measurement, i.e. one sensor arranged for measuring the component HN of the field normal to the surface inspected and one or two other sensors arranged for measuring the tangential component or components, $H_{T1}$ and $H_{T2}$, respectively in the main direction of the remanent field and in the perpendicular direction.

Figure 12:
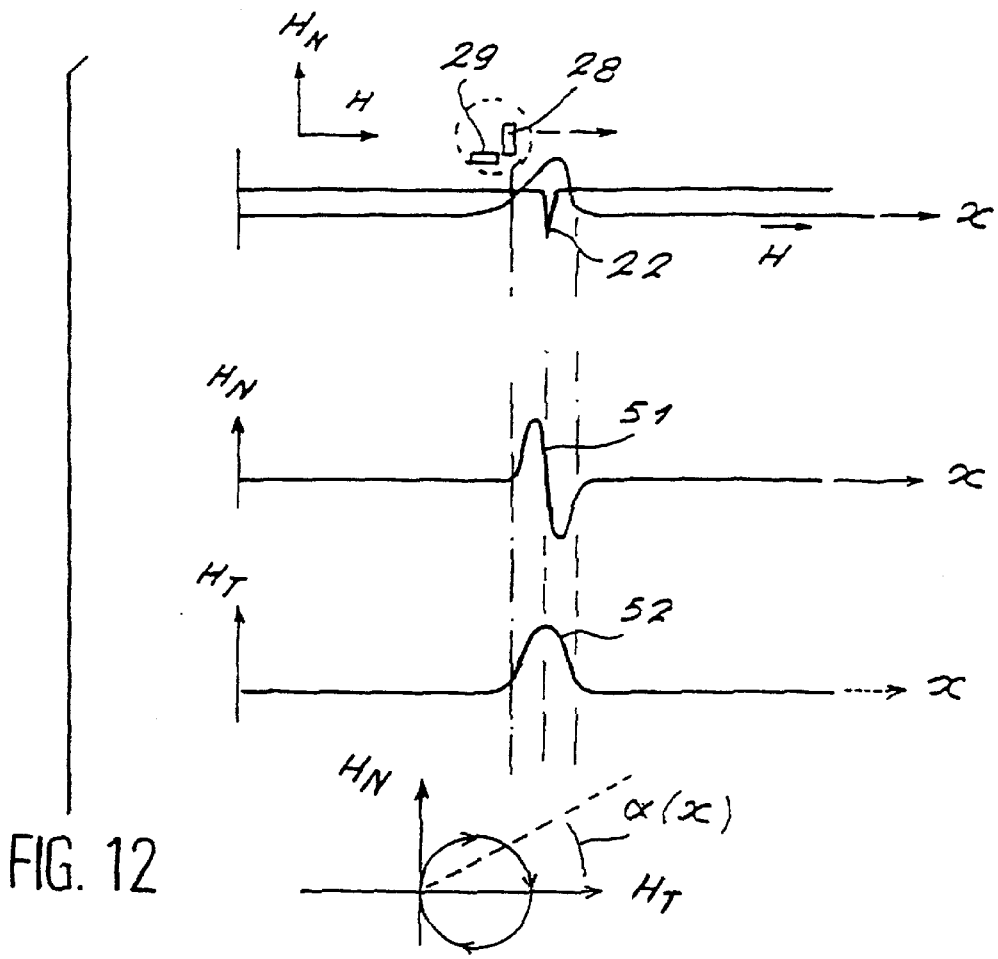
FIG. 12 represents the measurement of the two components of the remanent field in the presence of a fault in the layer to be inspected and the corresponding signals.

An example of the use of two sensors combined in this way is illustrated in FIG. 12. The sensor 28 is oriented so as to measure the normal component $H_N$ and the sensor 29 is oriented so as to measure the component $H_{T1}$ in the direction of movement of the sensors. The corresponding signals delivered by the sensors in the presence of a crack 22 are shown by curves S1 and S2 in FIG. 12, which also shows, by way of examples of the information which may thus be obtained on the fault 22, a graphical representation of the variations in $H_N$ as a function of $H_T$, making it possible to determine the orientation α(x) of the leakage flux with respect to the direction of movement x and therefore to characterize the type of fault detected.

Simultaneous measurements of two or three components of the field variations make it possible, in particular by suitable processing of the signals delivered by each of the sensors combined in this way, to obviate any perturbations arising from variations in the speed of movement of the sensors with respect to the pipe. Thus, in the case illustrated in FIG. 12, the function $H_N(H_{T1})$, which is independent of the speed of movement of the sensors, may be exploited directly without it being necessary to use selective filters, as would be the case for signals delivered as a function of time.

Figure 13:
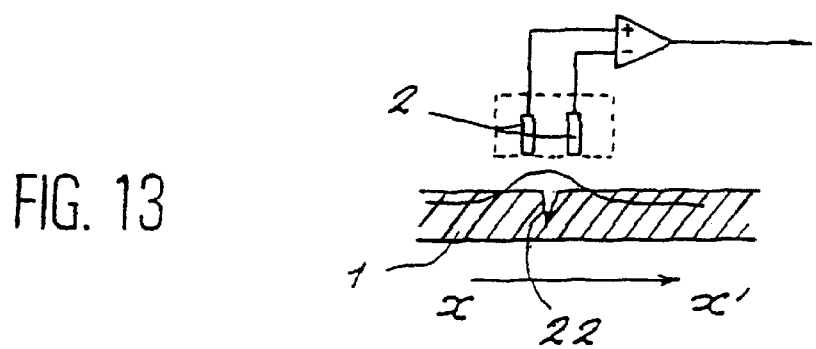
FIG. 13 illustrates an arrangement of the sensors for making differential measurements.

Two identical sensors may also be mounted side by side along the magnetization direction x–x', as shown in FIG. 13, in order to make differential measurements. Such a set-up, the principle of which is well-known, allows further improvement of the sensitivity and resolution by differentiating, along the magnetization direction x–x', the measured field. Other sensors may also be mounted in differential mode in a similar manner, these being oriented in the directions of the other components of the field. The distance between the two sensors of the same pair will be optimized depending on the geometry of the faults to be detected and on any periodic perturbations to be attenuated.

Figure 14:
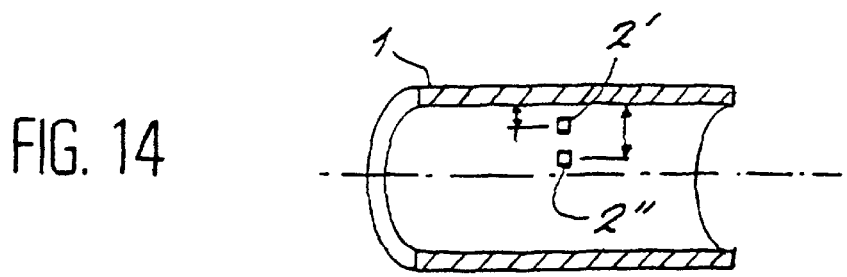
FIG. 14 illustrates another arrangement of the sensors, making it possible to reduce the influence of the variations in separation between them and the layer to be inspected.

Moreover, it will be possible to use, for each component of the field, a set of two sensors which are linked together and superposed along the radial direction of the pipe, as shown in FIG. 14. Such an arrangement makes it possible to reduce the influence of any variations in the air gap between the sensor and the layer to be inspected. This is because the sensor 2' closest to the wall is sensitive both to the faults and to the variations in this air gap, while the sensor 2" further away from the wall is practically only sensitive to these air-gap variations. It will be readily understood that the difference between the two signals obtained will make it possible to eliminate the perturbations due to these air-gap variations.

Optimum detection of the faults is again exposed to another problem resulting from the geometrical characteristics of the layer to be inspected. This is because, in the case of the flexible pipe in question, the regions of separation or interstice 26 between two successive turns 20 cause a distortion 27 of the flux lines 25, shown in FIG. 8, and therefore a leakage flux to which the sensor may be sensitive, the more so that, as indicated previously, the faults which it is desired preferably to detect are the longitudinal cracks in the zeta wire 20, and possible unlocking, and that, to this end, the preferred magnetization is oriented along the axis of the flexible pipe, and therefore, also transversely to the direction of the said joints. In order to eliminate, or at least limit, the effect of these distortions 27 of the flux lines due to the joints 26, high-pass filtering of the signal is carried out.

In fact as will be understood in the light of FIG. 8, the signals corresponding to these joints are more spread out than the signals from the cracks because of the fact that the width of these joints is conventionally greater (about 1 mm) than that of the cracks (a few tenths of a millimetre at most), which therefore cause a higher frequency signal.

Moreover, it has been observed that, despite the relatively large gap between these joints, the amplitude of the corresponding signals remains limited, something which has been explained by the fact that the rounded fillets of the cross-section of the shaped wire, for example the zeta profiled strip, and the contact between two adjacent turns, this contact being in the middle of the thickness of the vault layer, promote the guidance of the field lines towards the inside of this layer and therefore decrease the amplitude of the leakage flux caused by these joints compared to that which would be obtained with angular fillets, which is therefore favourable for detecting the cracks.

It will again be noted that the axial magnetization, as illustrated in FIG. 8 is particularly favourable for detecting longitudinal cracks in the profiled wire making up the vault 11, whether this wire be a profiled strip of the zeta type or any other type conventionally used for flexible pipes taken as an example, because of the fact that it makes it easier to detect such cracks oriented transversely to the said field and that it makes it possible, from measurements made along the circumference of the flexible pipe, to determine the length of such cracks. It has also been observed that this magnetization also makes it possible to detect transverse fractures in the wire.

Figure 10:
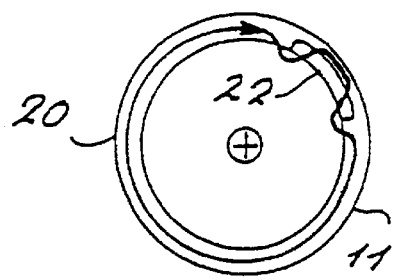
FIG. 10 illustrates the deflection of the field lines in the circumferential direction of the flexible pipe, in the presence of a circumferentially oriented crack, such as a longitudinal crack in such a vault wire.

As a variant, it is possible to induce a circumferentially oriented magnetization which makes it easier to identify transverse cracks in a small-pitched spiralled wire, such as the crack 21 in the wire 20, shown in FIG. 9. With regard to longitudinal cracks, which it has been stressed are important to be able to locate, it is possible to identify them by such a circumferential magnetization, in the case of a small-pitched spiralled wire, by means of the signals characterizing the two ends of the crack 22, as illustrated in FIG. 10.

Filtering adapted to the signals delivered by the sensors also makes it possible to improve fault detection. Thus, low-pass filtering makes it possible to eliminate the undesirable effect of possible faults in an intermediate layer, such as the carcass 13, which would not be completely nonmagnetic or demagnetized. This is because such faults, which are closer to the sensors, generate higher-frequency signals in them than faults further away because of the flattening of the deviations of the leakage flux lines which increases on moving away from the fault.

On the basis of the latter observation, and in order to further limit possible perturbations which could arise, despite the selective demagnetization described above, of such a slightly magnetic intermediate layer, or else to improve the effectiveness of the inspection in the case in which the remanent magnetization of the intermediate region is quite low in order not to carry out selective demagnetization, but in which it is sufficient to affect the inspection to a greater or lesser extent, the sensors will be moved slightly away from the surface of this layer, for example by from 0.5 mm to a few millimetres.

According to a preferred method of measuring and of processing the signals obtained, at least two components of the field are measured, either using an absolute measurement or using a differential measurement, and the signal obtained, which is representative of each component of the field measured, is processed by differentiation with respect to one or more spatial direction and mappings, representative of the sections of pipe, are produced which make it possible, for example, using known image-processing methods, to remove the spurious fault signals such as those which may arise from the separations between the wires of the vault, or to determine various characteristics of the faults, allowing them to be differentiated and sorted depending on their orientation, on their width or length, etc.

Although the above explanations have been given essentially within the context of the application of the invention to the inspection from inside the flexible pipes shown in FIG. 1, the invention is not limited to such an application. The inspection procedure and the inspection device, as defined in the claims, also apply to the inspection of the pressure vault of flexible pipes having another structure, for example one in which the vault is formed from wires having any cross-section, whether self-interlocking or not, or else to the inspection of the armouring layers formed by wires of ferromagnetic material, of any (flat, "T"-shaped, etc.) crosssection which are wound with a relatively long pitch, for example from wires inclined at 45°, in particular in the case of flexible pipes having armouring plies which also fulfil the function of resistance to the internal pressure forces, an internal pressure sheath made of polymer material and an internal carcass similar to that of the flexible pipes with a pressure vault.

Whatever the type of flexible pipe in question, the invention also applies when one or more intermediate layers, such as the carcass of the flexible pipes described previously, is made of a non-magnetic or slightly magnetic material, such as austenitic stainless steel or aluminium, or made of a magnetic material, such as ferritic stainless steel.

The invention also applies to the inspection, from the outside, of products having a more or less solid crosssection, such as the anchoring cables mentioned in the beginning of this specification, or of the tubular products mentioned above, for example for the inspection of the ferromagnetic armouring plies through an outer sheath made of polymer material and optionally one or more electrically insulating layers, such as an adhesive tape, thermal insulation foam, etc., or for the inspection, from the outside, of the ferromagnetic pressure vault of flexible pipes whose armouring plies are non-magnetic, for example made of a composite material based on glass fibres.

In such cases of inspection carried out from the outside on products which may be very long, it will be possible to use a device based on the same principle as that described previously for inspection from the inside, by producing the various heads or modules in an annular form suitable for encircling the product, each head or module preferably being formed by two shells which can be moved apart in order to make it easier to fit them around the product, transversely to its axis. These heads may be constructed in the form of individual modules introduced separately in a series of successive operations (by transposition of the procedure according to FIGS. 3 and 4) or in the form of a single autonomous inspection device which can be moved along the length of the pipe and consists of several annular modules coupled to each other by linkage elements (transposition of the device according to FIG. 15).

The invention thus applies to all elongate products, even very long ones, whether flexible or rigid, in which the inspection means cannot be moved into direct proximity with the layer to be inspected and/or in which the faults to be detected are far from the surface along which the said inspection means can be moved.

In its fundamental principle, the invention applies generally to any product having at least one layer of ferromagnetic material which comprises a region to be inspected, and having an accessible surface, the layer of ferromagnetic material being contained between two surfaces which are approximately parallel to the said accessible surface, and the region to be inspected being at some distance from the accessible surface and, moreover, sufficiently far from any edge which the layer of magnetic material could have, so as to avoid edge effects. The invention thus applies not only typically to elongate products but also to flat products such as, for example, large sheets, tanks or vessels, etc.

It will be noted that the extent of the area of the said region to be inspected may be either similar to the total area of the ferromagnetic layer (the difference in area corresponding, to a certain degree, to the end regions which are not inspectable because of the aforementioned edge effects) or less than the area of the ferromagnetic layer, for example if, between two separate regions to be inspected, there is a region excluded from inspection because of it having, locally, an excessive curvature.

Moreover, each region to be inspected may be regarded as being delimited by two surfaces approximately parallel to an intermediate predetermined surface which may be a plane surface, a cylindrical surface of revolution or a portion of a cylinder of revolution, or else a cylinder or part of a cylinder of curvature which varies in a progressive and relatively limited way.

As will have been understood, the invention is aimed at the inspection of the said region to be inspected which is at some distance from the said accessible surface, between which region and which surface the wall therefore has an intermediate region whose presence is the cause, on account of its thickness and of the properties of the materials of which it is composed, of some of the problems which magnetic inspection of the said region to be inspected poses and which the invention makes it possible to solve. The said intermediate region may include:

a non-magnetic layer which may be quite thick, of any shape, but which is between two surfaces parallel to the accessible surface and, consequently, parallel to the surfaces delimiting the layer made of magnetic material, and/or, a layer of slightly magnetic or ferromagnetic material, i.e. capable of retaining a remanent magnetization after the magnetizing step, this layer being separate from the ferromagnetic layer to be inspected, and/or, a region, which may be quite thick, lying within the ferromagnetic layer containing the region to be inspected, the said region to be inspected constituting that part of the ferromagnetic layer furthest away from the accessible surface (as may be the case, for example, with the inspection of thick steel pipes in which it is desired to detect faults lying deep within them).

We claim:

1. A device for the magnetic inspection of a long flexible pipe, wherein a wall of the flexible pipe includes at least one internal layer formed by a spiralled wire of ferromagnetic material, the device comprising:

magnetizing means for generating a localized magnetization field, the localized magnetization field generating, in the wall of the flexible pipe, a magnetic field oriented parallel to an accessible surface of the flexible pipe; and magnetic field measuring sensors arranged for measuring the magnetic field near the surface in several directions, wherein the magnetizing means and the magnetic field measuring sensors are coupled for movement along a longitudinal direction of the flexible pipe parallel to the surface, and wherein the magnetizing means and the magnetic field measuring sensors are, while they are being used, separated from each other by a distance such that the magnetization field generated by the magnetizing means is not to be directly measured by the magnetic field measuring sensors.

2. The device according to claim 1, further comprising a drive for alternately and successively moving the magnetizing means and the magnetic field measuring sensors along the surface of the flexible pipe.

3. The device according to claim 1, further comprising a drive coupled to the magnetizing means and the magnetic field measuring sensors for moving the magnetizing means and the magnetic field measuring sensors simultaneously along the surface of the flexible pipe.

4. The device according to claim 1, wherein the magnetizing means comprises a magnetization source having a north pole and a south pole and flexible elements for conducting the lines of magnetic flux, the flexible elements being fitted in the poles in order to be in contact with the surface of the flexible pipe.

5. The device according to claim 1, wherein the sensors further comprise a set of two sensors superimposed in the direction perpendicular to the surface of the wall.

6. The device according to claim 3, further comprising a demagnetizer lying upstream of the magnetizing means with respect to the magnetic field measuring sensors.

7. The device according to claim 3, further comprising a demagnetizing means coupled between the magnetizing means and the magnetic field measuring sensors.

8. A method for the magnetic inspection of a long flexible pipe, the wall of the pipe including at least one internal layer formed by a spiralled wire made of ferromagnetic material, the method comprising the steps of:

magnetizing the internal layer by a field oriented parallel to a surface of the wall, so as to generate a remanent magnetic field in the internal layer;

measuring several components of the remanent magnetic field near the surface of the wall, the components of the remanent magnetic field being oriented in different directions, wherein variations in the measured components of the remanent magnetic field are indicative of faults in the internal layer;

generating signals representative of each of the several measured components of the field;

detecting faults in the internal layer by processing the signals by differentiation as a function of one or more spatial direction; and mapping the detected faults, which are representative of the geometrical characteristics of the faults.

9. The method according to claim 8, further comprising the step of demagnetizing the wall before the internal layer is magnetized.

10. A method for the magnetic inspection of a long flexible pipe a flexible pipe, wherein a wall of the flexible pipe includes at least one internal layer formed by a spiralled wire made of ferromagnetic material, and wherein the wall further includes, between the internal layer to be inspected and an accessible surface of the flexible pipe, an intermediate layer which is not completely non-magnetic, the method comprising the steps of:

magnetizing the internal layer by a field oriented parallel to a surface of the wall, so as to generate a remanent magnetic field in the internal layer, selectively demagnetizing the intermediate layer after the magnetizing step; and measuring the remanent magnetic field near the surface of the wall, wherein variations in the measured remanent magnetic field are indicative of faults in the internal layer.

* * * * *